United States Patent [19]

Anderson

[11] 4,259,348

[45] Mar. 31, 1981

[54] PESTICIDAL ESTERS OF AMINO ACIDS

[75] Inventor: Richard J. Anderson, Palo Alto, Calif.

[73] Assignee: Zoecon Corporation, Palo Alto, Calif.

[21] Appl. No.: 145,924

[22] Filed: May 2, 1980

[51] Int. Cl.$^3$ .................. A01N 37/34; C07C 121/78
[52] U.S. Cl. ................................. 424/304; 260/465 D
[58] Field of Search ................... 260/465 D; 424/304

[56] References Cited

U.S. PATENT DOCUMENTS

| | | | |
|---|---|---|---|
| 4,161,537 | 7/1979 | Katsuda et al. | 424/304 |
| 4,176,195 | 11/1979 | Stoutamire | 424/304 |
| 4,201,787 | 5/1980 | Katsuda et al. | 424/304 |

FOREIGN PATENT DOCUMENTS 2812169 10/1978 Fed. Rep. of Germany .

*Primary Examiner*—Dolph H. Torrence
*Attorney, Agent, or Firm*—Donald W. Erickson

[57] ABSTRACT

A novel diastereomeric ester of an amino acid, synthesis thereof, and the use of said ester for the control of pests.

2 Claims, No Drawings

PESTICIDAL ESTERS OF AMINO ACIDS

This invention relates to a novel diastereomeric ester of an amino acid, synthesis thereof, and the use of said ester for the control of pests.

The compound of the present invention is represented by the following formula (A):

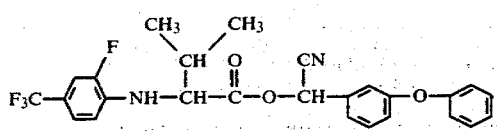

wherein,
the acid is the R configuration and the alcohol is the S configuration.

Certain esters of substituted-phenylamino acids have been described by Henrick & Garcia, Offenlegungsschrift 28 12 169, as being effective agents for the control of pests such as insects and acarids, acting in the manner of synthetic pyrethroids. The diastereomer of formula (A) herein has been found to possess greatly improved pesticidal activity as compared to the diastereomeric mixture, other diastereomers or the diastereomeric pairs.

As a generally applicable method of synthesis, the compounds of formula (A) can be prepared by the reaction of a racemic mixture of 2-(2-fluoro-4-trifluoromethylphenylamino)-3-methylbutanoic acid with the S enantiomer of α-cyano-3-phenoxybenzyl alcohol.

This esterification can be carried out at a low temperature in the presence of 4-dimethylaminopyridine and dicyclohexylcarbodiimide.

The S enantiomer of the alcohol is made by reacting racemic α-cyano-3-phenoxybenzyl alcohol with (R)-1-(1-naphthyl)-ethyl isocyanate in the presence of 4,4-dimethylaminopyridine and a solvent such as toluene or benzene. The resulting carbamate is separated into its two diastereomers by liquid chromatography. The R,R isomer is further purified by crystallization and the R,S isomer, by repeated chromatography. Alternatively, the diastereomers can be separated from the mixture without initial chromatographic separation by adding a seed crystal of substantially optically pure (R,R)-carbamate and crystallizing out the R,R isomer. The separated R,S diastereomer, in a solvent such as benzene, is reacted with trichlorosilane and triethylamine, at elevated temperature, to give the resulting S enantiomer of the alcohol.

Alternatively, the S enantiomer of the alcohol can be made by reacting racemic α-cyano-3-phenoxybenzyl alcohol with (S)-1-(1-naphthyl)ethyl isocyanate in place of (R)-1-(1-naphthyl)-ethyl isocyanate using the procedures described above.

α-Cyano-3-phenoxybenzyl alcohol is a labile molecule and stereoselective preparation or the resolution of the racemic alcohol has not previously been successful. Cf. Elliott et al., Pestic. Sci. 9:105-111 (1978).

The compounds of the present invention of formula A are highly active pesticides, particularly against insects and acarids. The diastereomer of the invention is unexpectedly more active than the diastereomeric mixture, other diastereomers or the diastereomeric pairs.

In the use of the compounds of the present invention for combating insects and acarids for the protection of agricultural crops, for example soybeans, cotton, alfalfa, etc., a compound of formula A together with a carrier is applied to the locus in a pesticidally effective amount. The carrier can be liquid or solid and include adjuvants such as wetting agents, dispersing agents and other surface active agents. The compound of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of the compound of formula A in the formulation can vary widely, generally within the range of about 0.01 percent to about 90.0 percent, by weight.

The compound of the present invention is effective on many different insects and on acarids. The compound is an effective control agent for insects such as mosquitoes, flies, aphids, weevils and acarids such as the spider mite and ticks. Among the pests against which the compound of the present invention is pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compound of the present invention can be used in combination with pyrethroid synergists and/or other pesticides such as the carbamates, phosphates and insect growth regulators, e.g. propoxur, carbaryl, naled, dichlorvos, methoprene, kinoprene, hydroprene, cyhexatin and resmethrin.

Herein, and in the appended claims, the first letter designation refers to the configuration of the acid and the second letter designation refers to the configuration of the alcohol. For example, the diastereomer designated "RS" refers to $R_{acid}$-$S_{alcohol}$.

The following examples are provided to illustrate the practice of the present invention. Temperature is given in degrees Centigrade. RT means room temperature.

EXAMPLE 1

To 446 mg (1.6 mmol) of racemic 2-(2-fluoro-4-trifluoromethylphenylamino)-3-methylbutanoic acid and 450 mg of ~80% purity (S)-α-cyano-3-phenoxybenzyl alcohol in 4.5 ml of dichloromethane, at ice bath temperature under a nitrogen atmosphere, is added 24 mg of 4-dimethylaminopyridine and 412 mg of dicyclohexylcarbodiimide. The reaction is maintained at ice bath temperature for 1 hour, after which pentane is added to the mixture and the solid is separated by filtration. The filtrate, including several pentane washes of the solid, is shaken against 5% hydrochloric acid, 2 M sodium carbonate and brine and is then dried over sodium sulfate. Solvent is removed and the product is purified by thin layer chromatography (tlc) on silica gel plates, developing in 25% ether/hexane, to give (S)-α-cyano-3-phenoxybenzyl (R,S)-2-(2-fluoro-4-trifluoromethylphenylamino)-3-methylbutanoate.

Synthesis of (S)-α-cyano-3-phenoxybenzyl alcohol is described in Applicant's co-pending application Ser. No. 142,518 filed Apr. 21, 1980.

EXAMPLE 2

The (S)-α-cyano-3-phenoxybenzyl (R,S)-2-(2-fluoro-4-trifluoromethylphenylamino)-3-methylbutanoate from Example 1 above is subjected to liquid chromatography (silica columns, 8% ether/hexane solvent, two recycles) to partially resolve the diastereomers; three fractions were collected.

The third fraction, enriched in the more polar RS diastereomer, is further purified by rotary thin layer chromatography, eluting with 7.5% ethyl acetate/hexane, to obtain further enriched RS compound. Several more purifications by rotary chromatography, eluting with 7.5% ethyl acetate/hexane, yield the more polar diastereomer, (S)-α-cyano-3-phenoxybenzyl (R)-2-(2-fluoro-4-trifluoromethylphenylamino)-3-methylbutanoate, specific rotation $[\alpha]_D^{25} = +62.8°$ (CHCl$_3$), diastereomeric purity=99.0%.

EXAMPLE 3

Comparative activity of the four diastereomers of α-cyano-3-phenoxybenzyl 2-(2-fluoro-4-trifluoromethylphenylamino)-3-methylbutanoate and of the prior art diastereomeric mixture of the compound was determined by testing for toxicity on insect pests.

A. Two groups of 10 each of 0-24 hr III instar *Heliothis virescens* larvae are treated with 1 μl of the test compound in acetone at different dosage rates by application to the dorsum of the thorax. Two groups of 10 each are treated identically with 1 μl acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control group using Abbott's formula. The toxicity is expressed as LD$_{50}$, which is the dosage, in μg per insect, required to kill 50% of the test insects. The results are presented in Table I.

B. Fifteen 72-hr-old adult female *Musca domestica* L. are anesthetized with ether vapor. These are then treated with 1 μl of the test compound diluted to different dosage rates in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The toxicities of the compounds, expressed as LD$_{50}$, are presented in Table I below.

TABLE I
ACTIVITY OF α-CYANO-3-PHENOXYBENZYL 2-(2-FLUORO-4-TRIFLUOROMETHYLPHENYLAMINO)-3-METHYLBUTANOATE, AS LD$_{50}$ (μg/INSECT)

| Compound | Diastereomer | H. virescens | M. domestica |
| --- | --- | --- | --- |
| A | RR | 0.182 | 0.594 |
| B | SR | 0.180 | 0.275 |
| C | SS | 0.712 | 0.482 |
| D | RS | 0.00591 | 0.0154 |
| E | RS,SR,RR,SS | 0.0177 | 0.0517 |

The results of the above tests show that compound D, (S)-α-cyano-3-phenoxybenzyl (R)-2-(2-fluoro-4-trifluoromethylphenylamino)-3-methylbutanoate, is more than three times as active as the diastereomeric mixture (R,S)-α-cyano-3-phenoxybenzyl (R,S)-2-(2-fluoro-4-trifluoromethylphenylamino)-3-methylbutanoate (compound E). The three other diastereomers are all much less active than the diastereomeric mixture.

What is claimed is:

1. The compound (S)-α-cyano-3-phenoxybenzyl (R)-2-(2-fluoro-4-trifluoromethylphenylamino)-3-methylbutanoate.

2. A method for controlling insects or acarids which comprises applying to said insect or acarid or their habitat a pesticidally effective amount of the diastereomer (S)-α-cyano-3-phenoxybenzyl (R)-2-(2-fluoro-4-trifluoromethylphenylamino)-3-methylbutanoate.

* * * * *